(12) United States Patent
Kraus

(10) Patent No.: US 7,909,870 B2
(45) Date of Patent: Mar. 22, 2011

(54) HEIGHT-ADJUSTABLE SPINAL IMPLANT AND OPERATING INSTRUMENT FOR THE IMPLANT

(75) Inventor: Kilian Kraus, Werneck (DE)

(73) Assignee: TPL - Kilian Kraus, Werneck (DE)

( * ) Notice: Subject to any disclaimer, the term of this patent is extended or adjusted under 35 U.S.C. 154(b) by 0 days.

(21) Appl. No.: 11/451,015

(22) Filed: Jun. 12, 2006

(65) Prior Publication Data

US 2006/0241762 A1 Oct. 26, 2006

Related U.S. Application Data

(63) Continuation of application No. PCT/EP2004/014060, filed on Dec. 10, 2004.

(30) Foreign Application Priority Data

Dec. 11, 2003 (DE) .................................. 103 57 926

(51) Int. Cl.
*A61F 2/44* (2006.01)

(52) U.S. Cl. ..................................... 623/17.11

(58) Field of Classification Search ............... 623/17.11, 623/17.15–17.16; 254/103, 220, 235–236, 254/425; 606/57, 61, 90
See application file for complete search history.

(56) References Cited

U.S. PATENT DOCUMENTS

| | | | |
|---|---|---|---|
| 1,486,723 A | 3/1924 | Bernson | |
| 1,645,570 A | 10/1927 | Anderson | |
| 2,702,453 A | 2/1955 | Mercier | |
| 3,987,499 A | 10/1976 | Scharbach et al. | |
| 4,502,160 A | 3/1985 | Moore et al. | |
| 4,611,582 A | * 9/1986 | Duff ................................ | 606/61 |
| 4,932,975 A | 6/1990 | Main et al. | |
| 4,961,740 A | 10/1990 | Ray et al. | |
| 5,026,373 A | 6/1991 | Ray et al. | |
| 5,055,104 A | 10/1991 | Ray | |
| 5,236,460 A | 8/1993 | Barber | |
| 5,246,458 A | 9/1993 | Graham | |
| 5,273,013 A | 12/1993 | Kubis et al. | |
| 5,571,192 A | 11/1996 | Schönhöffer | |
| 5,575,790 A | 11/1996 | Chen et al. | |
| 5,665,122 A | 9/1997 | Kambin | |
| 5,702,449 A | 12/1997 | McKay | |
| 5,723,013 A | 3/1998 | Jeanson et al. | |
| 5,772,661 A | 6/1998 | Michelson | |

(Continued)

FOREIGN PATENT DOCUMENTS

DE 3023942 C3 4/1983

(Continued)

*Primary Examiner* — Thomas C Barrett
*Assistant Examiner* — Nicholas Woodall
(74) *Attorney, Agent, or Firm* — Laurence A. Greenberg; Werner H. Stemer; Ralph E. Locher

(57) ABSTRACT

A height-adjustable implant for insertion between vertebrae, includes first and second sleeve parts which are rotationally fixed in coaxial alignment and interconnected in an axially displaceable manner. The first sleeve part has an internal thread. A nut is positioned coaxially in an inner space surrounded by the sleeve parts and is fixed to the second sleeve part so that it can rotate but is axially fixed. The nut has an external thread which engages in the internal thread of the first sleeve part. A toothed ring extends coaxially with the central longitudinal axis of the sleeve parts and is located on the nut. The second sleeve part has a radial access opening in the vicinity of the toothed ring.

12 Claims, 10 Drawing Sheets

U.S. PATENT DOCUMENTS

| | | | |
|---|---|---|---|
| 5,776,197 A | 7/1998 | Rabbe et al. | |
| 5,782,919 A | 7/1998 | Zdeblick et al. | |
| 5,885,299 A | 3/1999 | Winslow et al. | |
| 5,888,228 A | 3/1999 | Knothe et al. | |
| 5,904,719 A | 5/1999 | Errico et al. | |
| 5,951,553 A | 9/1999 | Betz et al. | |
| 5,980,522 A | 11/1999 | Koros et al. | |
| 5,989,290 A | 11/1999 | Harms et al. | |
| 6,004,326 A | 12/1999 | Castro et al. | |
| 6,015,436 A | 1/2000 | Schönhöffer | |
| 6,042,582 A | 3/2000 | Ray | |
| 6,077,267 A | 6/2000 | Huene | |
| 6,086,595 A | 7/2000 | Yonemura | |
| 6,086,613 A | 7/2000 | Camino et al. | |
| 6,113,638 A | 9/2000 | Williams et al. | |
| 6,120,503 A | 9/2000 | Michelson | |
| 6,129,763 A | 10/2000 | Chauvin et al. | |
| 6,156,040 A | 12/2000 | Yonemura et al. | |
| 6,176,881 B1 * | 1/2001 | Schar et al. | 623/17.11 |
| 6,190,413 B1 | 2/2001 | Sutcliffe | |
| 6,193,756 B1 | 2/2001 | Donno et al. | |
| 6,214,050 B1 | 4/2001 | Huene | |
| 6,267,763 B1 | 7/2001 | Castro | |
| 6,287,308 B1 | 9/2001 | Betz et al. | |
| 6,296,665 B1 | 10/2001 | Strnad et al. | |
| 6,299,644 B1 | 10/2001 | Vanderschot | |
| D450,122 S | 11/2001 | Michelson | |
| 6,315,795 B1 | 11/2001 | Scarborough et al. | |
| 6,315,975 B1 | 11/2001 | Lindblad | |
| 6,375,683 B1 | 4/2002 | Crozet et al. | |
| 6,395,034 B1 | 5/2002 | Suddaby | |
| 6,419,706 B1 | 7/2002 | Graf | |
| 6,428,575 B2 | 8/2002 | Koo et al. | |
| 6,436,142 B1 | 8/2002 | Paes et al. | |
| 6,443,989 B1 | 9/2002 | Jackson | |
| 6,443,990 B1 | 9/2002 | Aebi et al. | |
| 6,451,057 B1 | 9/2002 | Chen et al. | |
| 6,454,806 B1 | 9/2002 | Cohen et al. | |
| 6,454,807 B1 | 9/2002 | Jackson | |
| 6,471,724 B2 | 10/2002 | Zdeblick et al. | |
| 6,478,795 B1 | 11/2002 | Gournay et al. | |
| 6,511,484 B2 | 1/2003 | Torode et al. | |
| 6,520,991 B2 | 2/2003 | Huene | |
| 6,524,341 B2 * | 2/2003 | Lang et al. | 623/17.15 |
| 6,527,805 B2 | 3/2003 | Studer et al. | |
| 6,544,265 B2 | 4/2003 | Lieberman | |
| 6,551,319 B2 | 4/2003 | Lieberman | |
| 6,554,265 B2 | 4/2003 | Andronica | |
| 6,562,074 B2 | 5/2003 | Gerbec et al. | |
| 6,576,016 B1 | 6/2003 | Hochshuler et al. | |
| 6,579,290 B1 | 6/2003 | Hardcastle et al. | |
| 6,582,432 B1 | 6/2003 | Michelson | |
| 6,582,468 B1 | 6/2003 | Gauchet | |
| 6,641,614 B1 | 11/2003 | Wagner et al. | |
| 6,695,760 B1 | 2/2004 | Winkler et al. | |
| 6,706,070 B1 | 3/2004 | Wagner et al. | |
| 6,719,796 B2 | 4/2004 | Cohen et al. | |
| 6,730,088 B2 | 5/2004 | Yeh | |
| 6,749,613 B1 | 6/2004 | Conchy et al. | |
| 6,752,832 B2 | 6/2004 | Neumann | |
| 6,758,862 B2 | 7/2004 | Berry et al. | |
| 6,758,863 B2 | 7/2004 | Estes et al. | |
| 6,766,798 B2 | 7/2004 | Herres et al. | |
| 6,776,798 B2 | 8/2004 | Camino et al. | |
| 6,779,353 B2 | 8/2004 | Hu et al. | |
| 6,783,526 B1 | 8/2004 | Lin et al. | |
| 6,783,528 B2 | 8/2004 | Vincent-Prestigiacomo | |
| 6,783,547 B2 | 8/2004 | Castro | |
| 6,796,984 B2 | 9/2004 | Soubeiran | |
| 6,808,537 B2 | 10/2004 | Michelson | |
| 6,814,756 B1 | 11/2004 | Michelson | |
| 6,830,589 B2 | 12/2004 | Erickson | |
| 6,835,206 B2 | 12/2004 | Jackson | |
| 6,852,129 B2 | 2/2005 | Gerbec et al. | |
| 6,855,168 B2 | 2/2005 | Crozet | |
| 6,863,673 B2 | 3/2005 | Gerbec et al. | |
| 6,866,664 B2 | 3/2005 | Schär et al. | |
| 6,866,682 B1 * | 3/2005 | An et al. | 623/17.15 |
| 6,896,512 B2 | 5/2005 | Rattner et al. | |
| 6,899,734 B2 | 5/2005 | Castro et al. | |
| 6,905,512 B2 | 6/2005 | Paes et al. | |
| 6,921,403 B2 | 7/2005 | Cragg et al. | |
| 6,923,810 B1 | 8/2005 | Michelson | |
| 6,923,830 B2 | 8/2005 | Michelson | |
| 6,955,691 B2 | 10/2005 | Chae et al. | |
| 6,960,232 B2 | 11/2005 | Lyons et al. | |
| 6,976,949 B2 | 12/2005 | Winkler et al. | |
| 6,979,353 B2 | 12/2005 | Bresina | |
| 6,991,653 B2 | 1/2006 | White et al. | |
| 6,991,654 B2 | 1/2006 | Foley | |
| 7,008,453 B1 | 3/2006 | Michelson | |
| 7,018,412 B2 | 3/2006 | Ferreira et al. | |
| 7,018,415 B1 | 3/2006 | McKay | |
| 7,022,138 B2 | 4/2006 | Mashburn | |
| 7,025,787 B2 | 4/2006 | Bryan et al. | |
| 7,029,498 B2 | 4/2006 | Boehm et al. | |
| 7,033,392 B2 | 4/2006 | Schmiel et al. | |
| 7,094,257 B2 | 8/2006 | Mujwid et al. | |
| 7,097,648 B1 | 8/2006 | Globerman et al. | |
| 7,118,590 B1 | 10/2006 | Cronin | |
| 7,118,598 B2 | 10/2006 | Michelson | |
| 7,147,665 B1 | 12/2006 | Bryan et al. | |
| 7,156,874 B2 | 1/2007 | Paponneau et al. | |
| 7,166,130 B2 | 1/2007 | Feree | |
| 7,166,131 B2 | 1/2007 | Studer et al. | |
| 7,182,781 B1 | 2/2007 | Bianchi et al. | |
| 7,192,446 B2 | 3/2007 | Shapiro et al. | |
| 7,192,496 B2 | 3/2007 | Wojcik | |
| 7,217,291 B2 | 5/2007 | Zucherman et al. | |
| 7,235,105 B2 | 6/2007 | Jackson | |
| 7,255,714 B2 | 8/2007 | Malek | |
| 7,273,498 B2 | 9/2007 | Bianchi et al. | |
| 7,282,063 B2 | 10/2007 | Cohen et al. | |
| 7,285,134 B2 | 10/2007 | Berry et al. | |
| 7,285,135 B2 | 10/2007 | McKay et al. | |
| 7,303,583 B1 | 12/2007 | Schär et al. | |
| 7,303,584 B2 | 12/2007 | Castro et al. | |
| 7,309,358 B2 | 12/2007 | Berry et al. | |
| 7,311,733 B2 | 12/2007 | Metz-Stavenhagen | |
| 7,316,686 B2 | 1/2008 | Dorchak et al. | |
| 7,320,708 B1 | 1/2008 | Bernstein | |
| 7,322,982 B2 | 1/2008 | Vincent-Prestigiacomo | |
| 7,329,283 B2 | 2/2008 | Estes et al. | |
| 7,331,994 B2 | 2/2008 | Gordon et al. | |
| 7,335,200 B2 | 2/2008 | Carli | |
| 7,364,589 B2 | 4/2008 | Eisermann | |
| 7,381,178 B2 | 6/2008 | Winkler et al. | |
| 7,384,431 B2 | 6/2008 | Berry | |
| 7,402,176 B2 | 7/2008 | Malek | |
| 7,407,513 B2 | 8/2008 | Alleyne et al. | |
| 7,410,501 B2 | 8/2008 | Michelson | |
| 2001/0012966 A1 | 8/2001 | Studer et al. | |
| 2001/0031965 A1 | 10/2001 | Zucherman et al. | |
| 2001/0056302 A1 | 12/2001 | Boyer, II et al. | |
| 2002/0010511 A1 | 1/2002 | Michelson | |
| 2002/0022887 A1 * | 2/2002 | Huene | 623/17.16 |
| 2002/0068976 A1 | 6/2002 | Jackson | |
| 2002/0068977 A1 | 6/2002 | Jackson | |
| 2002/0068978 A1 | 6/2002 | Camino et al. | |
| 2002/0082695 A1 | 6/2002 | Neumann | |
| 2003/0045877 A1 | 3/2003 | Yeh | |
| 2003/0108272 A1 | 6/2003 | Sherrer et al. | |
| 2003/0114854 A1 | 6/2003 | Pavlov et al. | |
| 2003/0130739 A1 | 7/2003 | Gerbec et al. | |
| 2003/0176925 A1 | 9/2003 | Paponneau | |
| 2003/0191535 A1 | 10/2003 | Castro | |
| 2003/0191555 A1 | 10/2003 | Takehara et al. | |
| 2003/0208272 A1 | 11/2003 | Crozet et al. | |
| 2004/0044411 A1 | 3/2004 | Suddaby | |
| 2004/0054412 A1 | 3/2004 | Gerbec et al. | |
| 2004/0073314 A1 | 4/2004 | White | |
| 2004/0153156 A1 | 8/2004 | Cohen et al. | |
| 2004/0153160 A1 | 8/2004 | Carrasco | |
| 2004/0167626 A1 | 8/2004 | Geremakis et al. | |
| 2004/0172129 A1 | 9/2004 | Schäfer et al. | |
| 2004/0210312 A1 * | 10/2004 | Neumann | 623/17.11 |
| 2004/0225366 A1 | 11/2004 | Eisermann et al. | |

| | | | |
|---|---|---|---|
| 2004/0249466 A1 | 12/2004 | Liu et al. | |
| 2004/0267364 A1 | 12/2004 | Carli et al. | |
| 2005/0004572 A1 | 1/2005 | Biedermann et al. | |
| 2005/0027359 A1 | 2/2005 | Mashburn | |
| 2005/0033437 A1 | 2/2005 | Bao et al. | |
| 2005/0060036 A1 | 3/2005 | Schultz et al. | |
| 2005/0060037 A1 | 3/2005 | Michelson | |
| 2005/0143820 A1 | 6/2005 | Zucherman et al. | |
| 2005/0143821 A1 | 6/2005 | Zdeblick et al. | |
| 2005/0143825 A1 | 6/2005 | Enayati | |
| 2005/0209697 A1 | 9/2005 | Paponneau et al. | |
| 2005/0228500 A1 | 10/2005 | Kim et al. | |
| 2006/0058877 A1 | 3/2006 | Gutlin et al. | |
| 2006/0058879 A1 | 3/2006 | Metz-Stavenhagen | |
| 2006/0069442 A1 | 3/2006 | Michelson | |
| 2006/0100710 A1* | 5/2006 | Gutlin et al. | 623/17.15 |
| 2006/0116770 A1 | 6/2006 | White et al. | |
| 2006/0129241 A1 | 6/2006 | Boyer et al. | |
| 2006/0149385 A1 | 7/2006 | McKay | |
| 2006/0200244 A1 | 9/2006 | Assaker | |
| 2006/0241770 A1* | 10/2006 | Rhoda et al. | 623/17.15 |
| 2007/0028710 A1 | 2/2007 | Kraus et al. | |
| 2007/0106385 A1 | 5/2007 | Zucherman et al. | |
| 2007/0168036 A1 | 7/2007 | Ainsworth et al. | |
| 2007/0191951 A1 | 8/2007 | Branch, Jr. | |
| 2007/0191954 A1* | 8/2007 | Hansell et al. | 623/17.15 |
| 2007/0255407 A1* | 11/2007 | Castleman et al. | 623/17.11 |
| 2008/0015698 A1 | 1/2008 | Marino et al. | |
| 2008/0015700 A1 | 1/2008 | Zucherman et al. | |
| 2008/0021560 A1 | 1/2008 | Zucherman et al. | |
| 2008/0021561 A1 | 1/2008 | Zucherman et al. | |
| 2008/0027552 A1 | 1/2008 | Zucherman et al. | |
| 2008/0027553 A1 | 1/2008 | Zucherman et al. | |
| 2008/0033445 A1 | 2/2008 | Zucherman et al. | |
| 2008/0039853 A1 | 2/2008 | Zucherman et al. | |
| 2008/0039858 A1 | 2/2008 | Zucherman et al. | |
| 2008/0039859 A1 | 2/2008 | Zucherman et al. | |
| 2008/0039945 A1 | 2/2008 | Zucherman et al. | |
| 2008/0039946 A1 | 2/2008 | Zucherman et al. | |
| 2008/0046088 A1 | 2/2008 | Zucherman et al. | |
| 2008/0046089 A1 | 2/2008 | Zucherman et al. | |
| 2008/0051904 A1 | 2/2008 | Zucherman et al. | |
| 2008/0051905 A1 | 2/2008 | Zucherman et al. | |
| 2008/0054904 A1 | 3/2008 | Neufeld et al. | |
| 2008/0058941 A1 | 3/2008 | Zucherman et al. | |
| 2008/0065086 A1 | 3/2008 | Zucherman et al. | |
| 2008/0071378 A1 | 3/2008 | Zucherman et al. | |
| 2008/0103602 A1 | 5/2008 | Berry et al. | |
| 2008/0172057 A1 | 7/2008 | Zucherman et al. | |
| 2008/0183210 A1 | 7/2008 | Zucherman et al. | |

FOREIGN PATENT DOCUMENTS

| | | |
|---|---|---|
| DE | 3023942 C2 | 5/1985 |
| DE | 3729600 A1 | 3/1989 |
| DE | 3729600 C2 | 9/1989 |
| DE | 69317654 T2 | 2/1995 |
| DE | 4423257 A1 | 1/1996 |
| DE | 195 19 101 A1 | 11/1996 |
| DE | 69317654 T2 | 10/1998 |
| DE | 198 16 782 A1 | 10/1999 |
| DE | 19841252 A1 | 3/2000 |
| DE | 19841252 B4 | 3/2000 |
| DE | 44 23 257 C2 | 7/2001 |
| DE | 201 09 599 U1 | 9/2001 |
| DE | 101 27 924 C1 | 9/2002 |
| DE | 100 65 232 C2 | 11/2002 |
| DE | 102 10 214 A1 | 9/2003 |
| DE | 19841252 B4 | 1/2006 |
| DE | 19622827 B4 | 4/2009 |
| EP | 0144667 A1 | 6/1985 |
| EP | 0144667 B1 | 5/1988 |
| EP | 0716840 A2 | 6/1996 |
| EP | 0716840 B1 | 5/2002 |
| EP | 1501453 A1 | 2/2005 |
| WO | 9857601 | 12/1998 |
| WO | 0023013 | 4/2000 |
| WO | 0024327 | 5/2000 |
| WO | 0172246 A1 | 10/2001 |

* cited by examiner

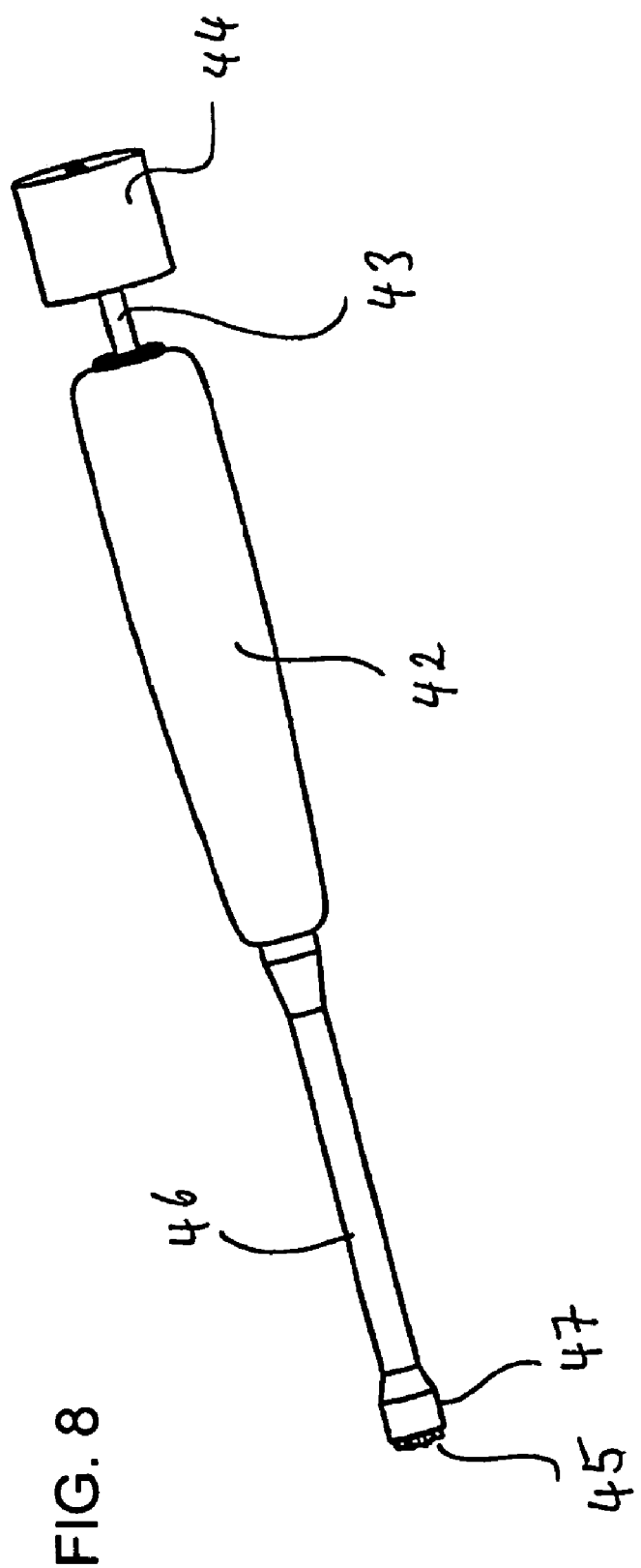

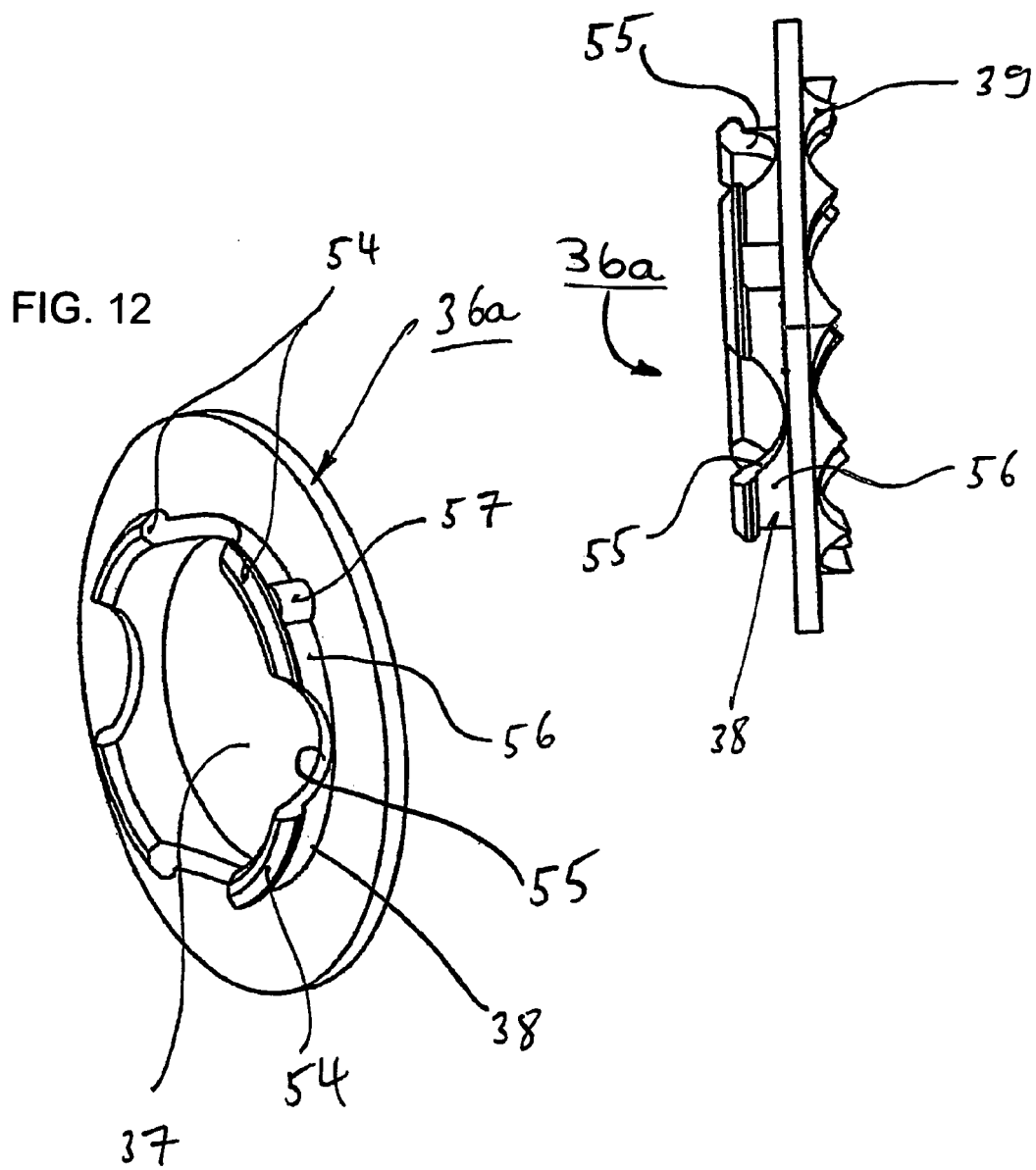

HEIGHT-ADJUSTABLE SPINAL IMPLANT AND OPERATING INSTRUMENT FOR THE IMPLANT

CROSS-REFERENCE TO RELATED APPLICATIONS

This is a continuing application, under 35 U.S.C. §120, of copending International Application No. PCT/EP2004/014060, filed Dec. 10, 2004, which designated the United States; this application also claims the priority, under 35 U.S.C. §119, of German Patent Application DE 103 57 926.5, filed Dec. 11, 2003; the prior applications are herewith incorporated by reference in their entirety.

BACKGROUND OF THE INVENTION

Field of the Invention

The invention relates to a height-adjustable or length-adjustable implant for insertion between vertebral bodies. The invention also relates to an operating instrument suitable for adjusting the implant.

Implants which are known, for example, from German Published, Non-Prosecuted Patent Application DE 196 22 827 A1, corresponding to U.S. Pat. No. 6,015,436, and U.S. patent application Publication Ser. No. US 2003/0045877 A1, have a first and a second sleeve part. The two sleeve parts are oriented coaxially and connected in a rotationally fixed and axially displaceable manner, and the first sleeve part has an external thread. In order to permit axial adjustment of the two sleeves relative to one another, a nut is provided which is secured rotatably on the second sleeve part and engages with its thread in the external thread of the first sleeve part. The two sleeve parts are moved axially relative to one another by rotating the nut. In order to rotate the nut, a rod-shaped operating instrument is inserted into a recess on the outer circumference of the nut. The nut is rotated by a distance corresponding to the pivot angle of the instrument through the use of a pivoting movement of the instrument in a plane extending transversely with respect to the longitudinal axis of the implant. Thereafter, the instrument has to be removed again from the nut and the procedure has to be repeated until the implant has a length that spans the space between two vertebral bodies. During the rotation of the nut, the second sleeve part must not be rotated along with it, so that the latter generally has to be held in place using a further instrument. The length adjustment in the known implants thus requires considerable expenditure in terms of time and equipment. In addition, a relatively large operating opening is needed to allow those manipulations to be performed without obstruction, in particular the pivoting of the operating instrument. A further disadvantage of the known implants is that surrounding tissue can be damaged both by the pivoting movement of the instrument as well as by the rotation movement of the nut. German Published, Non-Prosecuted Patent Application DE 101 27 924 A1 discloses an implant which has a similar structure to those described above. The rotation movement for height adjustment is effected by a gear unit. The gear unit includes a worm which is fitted onto the side of the implant and which can be activated with the aid of an operating instrument.

SUMMARY OF THE INVENTION

It is accordingly an object of the invention to provide a height-adjustable spinal implant and an operating instrument for the implant, which overcome the hereinafore-mentioned disadvantages of the heretofore-known devices of this general type and which make available an implant with improved handling and with a larger inner space for receiving bone material.

With the foregoing and other objects in view there is provided, in accordance with the invention, a height-adjustable implant for insertion between vertebral bodies. The implant comprises a first sleeve part having an internal thread and a second sleeve part having an access opening extending radially therethrough. The first and second sleeve parts are coaxially oriented about a central longitudinal axis and define an inner space therebetween, are connected to one another in a rotationally fixed and axially displaceable manner and have axially extending windows therein with mutually-facing, outwardly-open ends. Each adjacent two of the windows form a respective circumferential section therebetween in each of the sleeve parts. The circumferential sections of each one of the sleeve parts each fits axially displaceably into a respective one of the windows of the other of the sleeve parts. A nut is disposed coaxially in the inner space and secured on the second sleeve part in a rotatable but axially fixed manner. The nut has an external thread engaging in the internal thread of the first sleeve part. A toothed ring extends coaxially relative to the central longitudinal axis and is disposed on the nut in vicinity of the access opening.

The first advantage of this configuration is that no pivoting movements have to be performed with an operating instrument in order to rotate the nut. Instead, it is now possible for the operating instrument to be kept in one and the same position and orientation during the entire procedure of adjusting the length of the implant, which fact greatly simplifies the operation and reduces the operating time. Moreover, only a relatively small operating opening is now needed. The driving action can be effected in a simple manner, for example using a driving toothed wheel disposed at one end of an operating instrument. Another important advantage of the proposed implant is that the nut is disposed in the inner space of the implant, with the result that, when the nut is rotated, there is no risk of damage to the surrounding tissue. This applies also to a toothed wheel of the operating instrument that meshes with the toothed ring during the length adjustment. Damage to the surrounding tissue by the two sleeve parts moving axially relative to one another can in practice be excluded by virtue of their smooth outer surface.

The access opening not only ensures unobstructed access to the toothed ring, but also serves for securing an operating instrument on the implant. The corresponding end of the instrument is constructed in such a way that it can be secured in the access opening, e.g. can be inserted with an exact fit into the latter or can be screwed into it. The implant is then connected securely to the operating instrument, so that the latter can be used not only for rotating the nut but also for secure and positionally exact insertion of the implant into the spinal column. Moreover, this configuration ensures that the second sleeve part is fixed in terms of rotation during the adjustment of the implant length. Therefore, in contrast to conventional implants, only a single instrument is needed for driving the nut, for inserting the implant, and for fixing the second sleeve part in terms of rotation.

The axially extending windows of the two sleeve parts are also particularly advantageous. As compared to a configuration in which two sleeve parts with different diameters engage concentrically one inside the other, this configuration first of all has the advantage of saving material and reducing weight. Moreover, a larger inner space is available that can be filled with bone material or the like. The meshed engagement of the two sleeve parts also ensures that they are mutually fixed in terms of rotation.

In accordance with another feature of the invention, the toothed ring is constructed in the manner of a crown wheel. In this way, the drive pinion of the operating instrument can interact with the toothed ring in the manner of a contrate gear. This affords the advantage that the axis of rotation of the driving toothed wheel of an operating instrument runs approximately radially with respect to the central longitudinal axis of the implant and, accordingly, in the longitudinal direction of an expediently rod-shaped operating instrument. The latter can therefore be constructed in a relatively simple way, specifically by just having a centrally disposed rotation shaft with a driving toothed wheel secured on its end for rotating the nut.

In accordance with a further feature of the invention, the engagement of the nut in the internal thread of the first sleeve part is preferably ensured by its being secured on the second sleeve part in such a way that its external thread, seen in the axial direction, is located outside the second sleeve part. A configuration of the nut is also conceivable in which its thread, again seen in the axial direction, is located inside the second sleeve part. In order to allow it to engage in the thread of the nut, the internal thread of the first sleeve part would then have to protrude past the inside face of the second sleeve part, for example by its having a greater wall thickness than the second sleeve part. In the preferred configuration of the nut, however, such a measure is not necessary.

In accordance with an added feature of the invention, the toothed ring is preferably disposed on a surface of the nut facing away from the external thread, which is advantageous from a production point of view. Moreover, the length of the nut can be kept short. If the toothed ring were disposed on a surface facing toward the external thread, a greater axial distance would have to be present between the external thread and the toothed ring, namely at least an axial distance corresponding to the diameter of a driving toothed wheel that engages the toothed ring.

In accordance with an additional feature of the invention, disposed on the inside faces of each of the circumferential sections of the first sleeve part is a radially inwardly extending projection which engages in a circumferential groove of the nut in order to fix the nut axially. In this way, it is possible to ensure that the nut is secured axially, even in the case where it is subjected to loading. In order to assemble the nut on the first sleeve part, it is placed onto the latter. It is true that the sleeve part is made of a solid material, in particular of metal. However, the circumferential sections separated from one another in the circumferential direction have such an elasticity that they are deflected inward when the nut is fitted in place and then spring back again to their original state, with the projections snapping into the circumferential groove of the nut. The positioning of the projections near the free end of the circumferential sections has the advantage of permitting the nut to be kept relatively short, without thereby reducing the maximum path of adjustment of the implant. This configuration also saves material and reduces weight and it also increases the size of the inner space of the implant.

In accordance with yet another feature of the invention, in order to increase the size of the support surface of the implant, a radially widened support plate is provided which, in a preferred embodiment, is a separate part that can be secured on a sleeve part in a releasable manner. It is then possible, in each individual case, to use the appropriate support plate, for example one with a plane extending obliquely with respect to the central longitudinal axis of the implant. A support plate which is secured pivotably on a sleeve part is also conceivable. It can also advantageously be fixed in terms of rotation, for example in order to prevent a situation where an implant inserted between two vertebrae maintains its rotation position relative to the vertebral bodies or spinal column when the toothed ring is rotated. This fixing in terms of rotation is preferably achieved by several recesses, spaced apart in the circumferential direction and opening into the inside face of the sleeve part, being present in an end face of a sleeve part, and by projections of complementary shape on the support plate engaging in the recesses.

With the objects of the invention in view, there is also provided an operating instrument for an implant. The operating instrument comprises a handgrip and a shaft extending through the handgrip. The shaft has one end carrying a rotary grip and another end carrying a toothed wheel for engaging the implant. An implant can be easily and safely manipulated using such an instrument.

In accordance with another mode of the invention, the section of the shaft extending between the toothed wheel and the hand grip runs inside a jacket tube. This means that it cannot come into contact with tissue in the operating site, which could lead to undesired complications.

In accordance with a concomitant mode of the invention, the jacket tube also serves to secure the operating instrument on the implant. For this purpose, its front end facing toward the toothed wheel is constructed in such a way that it can be secured in the access opening of the implant, for example by being inserted into the latter with an exact fit or by being screwed into it.

Other features which are considered as characteristic for the invention are set forth in the appended claims.

Although the invention is illustrated and described herein as embodied in a height-adjustable spinal implant and an operating instrument for the implant, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWINGS

FIG. 8 is a perspective view of an operating instrument for manipulating an implant;

FIGS. 12 and 12A are respective perspective and side-elevational views of a support plate that can be secured on the implant of FIG. 2.

DESCRIPTION OF THE PREFERRED EMBODIMENTS

Figure 1:
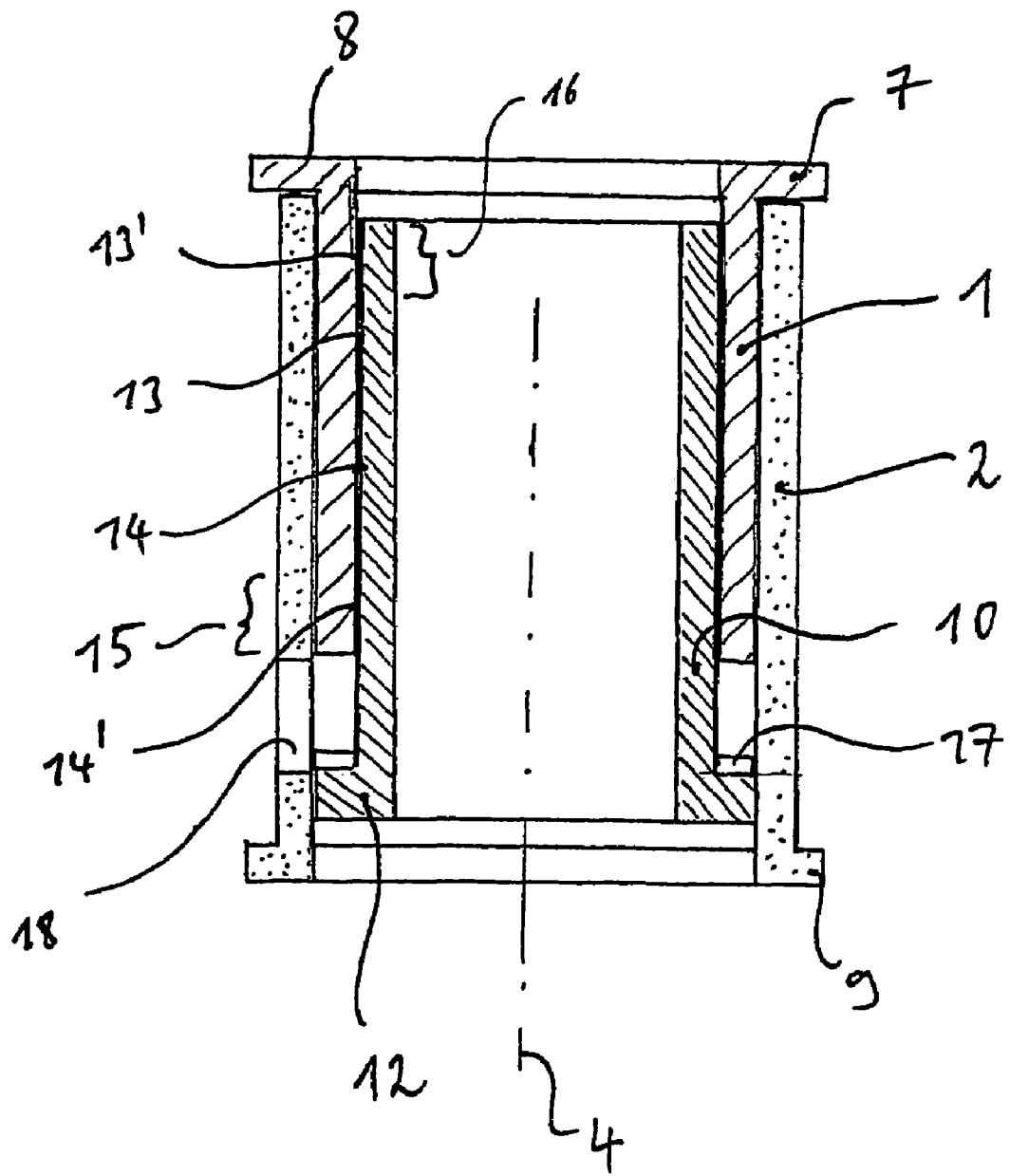
FIG. 1 is a diagrammatic, cross-sectional view of a first illustrative embodiment of a length-adjustable implant which includes, as its main components, a first and a second sleeve part and a nut.
Figure 2:
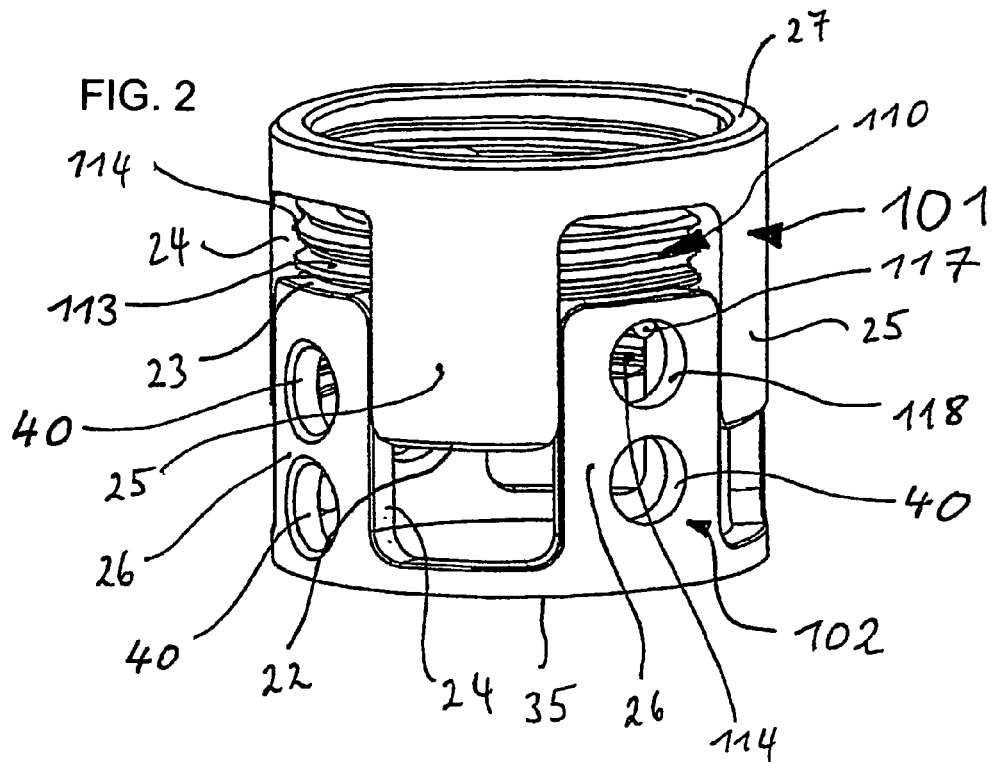
FIG. 2 is a perspective view of a second illustrative embodiment of an implant, likewise including the main components.
Figure 3:
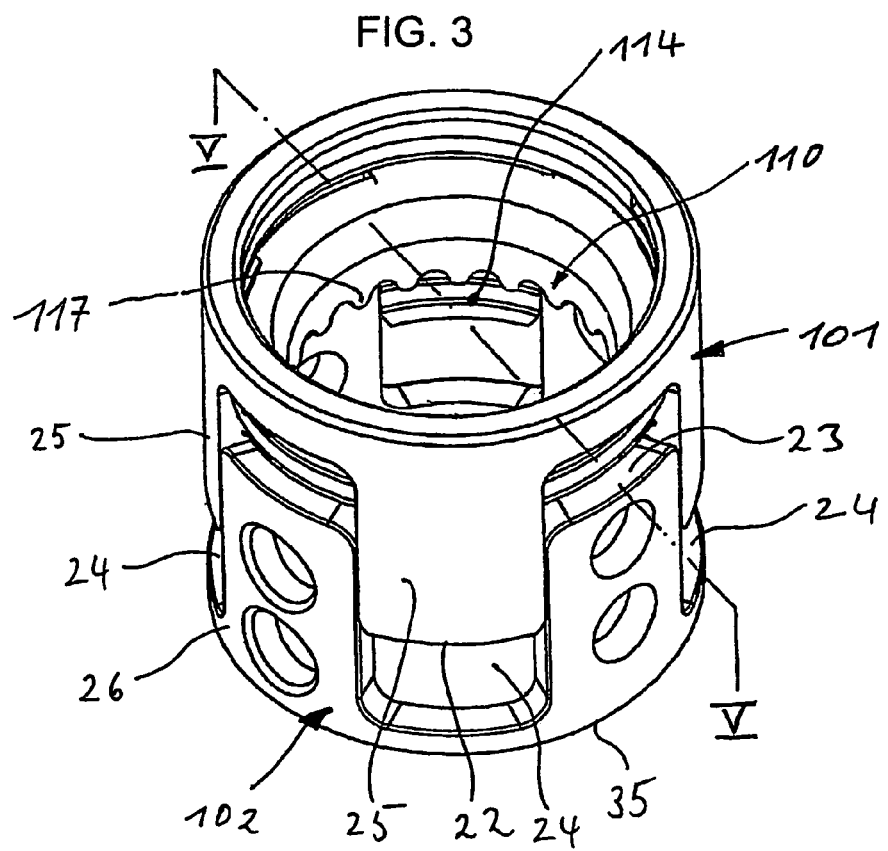
FIG. 3 is a perspective view of the implant of FIG. 2, viewed from another angle.
Figure 4:
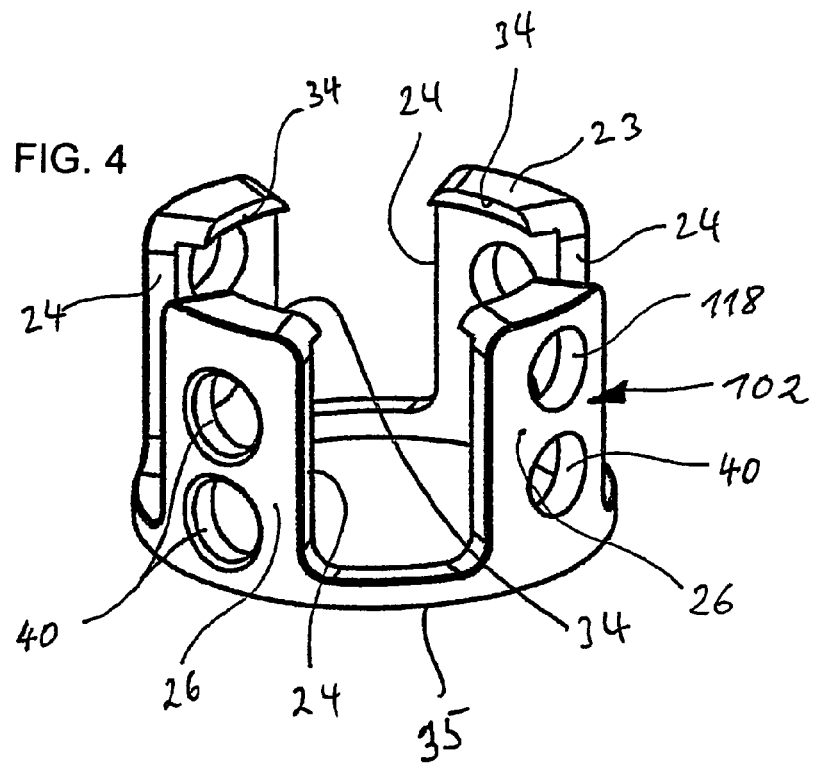
FIG. 4 is a perspective view of a second sleeve part of the implant of FIG. 2.
Figure 5:
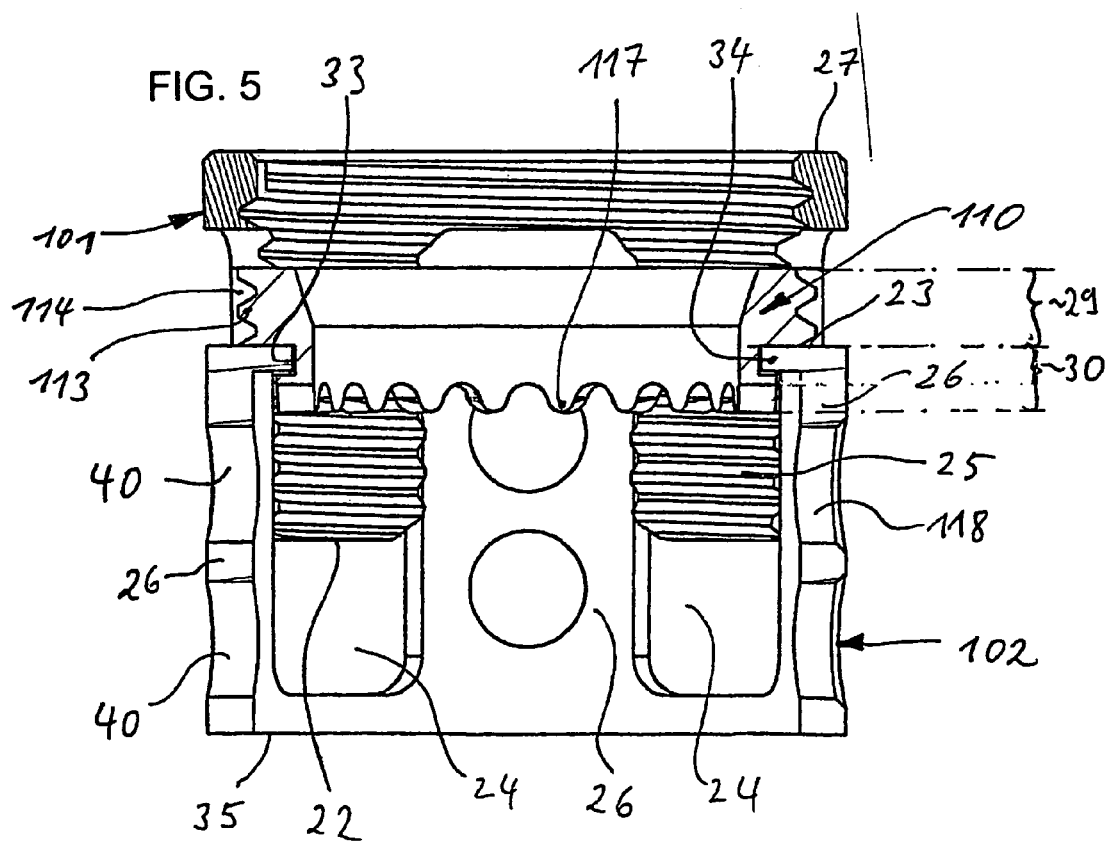
FIG. 5 is a cross-sectional view taken along a line V-V in FIG. 3.
Figure 6:
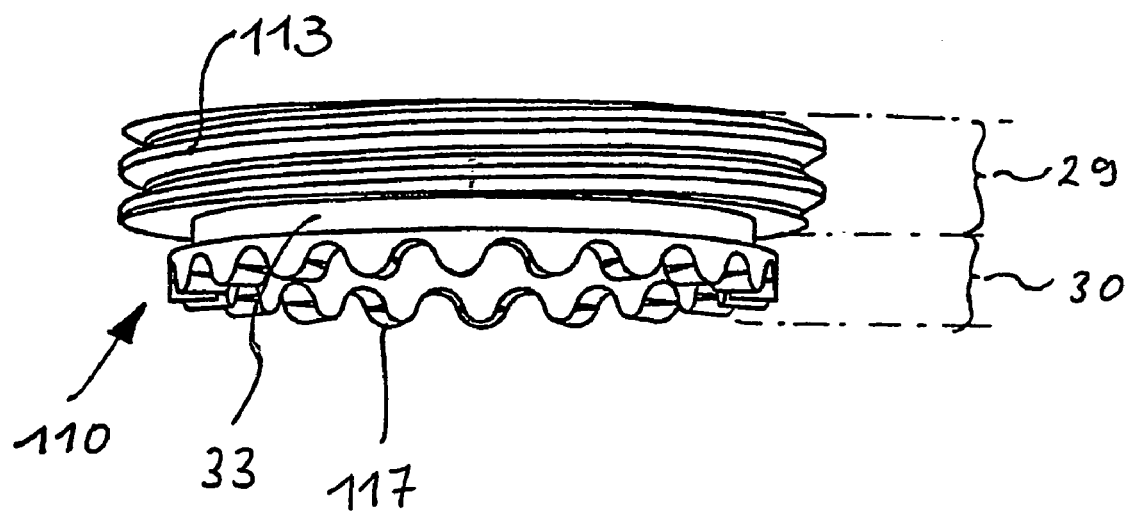
FIG. 6 is a perspective view of a nut.

It is initially noted that in order to simplify matters, the implants shown in the figures, each with a first sleeve part 1, 101, a second sleeve part 2, 102 and a nut 10, 110, will be described with reference to a vertically oriented implant that rests with its first sleeve part on a support base. Referring now to the figures of the drawings in detail and first, particularly, to FIG. 1 thereof, there is seen an illustrative embodiment in which the two sleeve parts 1, 2 are coaxial to one another and are fitted one inside the other in such a way that they are displaceable in a telescopic manner in the direction of their central longitudinal axis 4. The internal diameter of the sleeve part 2 is slightly greater than the external diameter of the sleeve part 1, such that the sleeve parts cooperate in the manner of a slide pairing in the event of a relative axial displacement. An end section of the sleeve part 1 protruding from the sleeve part 2 carries a radially outwardly directed flange 7 having an upper face 8 directed away from the sleeve part 2 which forms a support surface. The flange 7 additionally serves as an end abutment for the insertion movement of the sleeve part 1 into the sleeve part 2. A flange 9 serving the same purpose is likewise disposed at a lower end face of the sleeve part 2 directed away from the flange 7.

The two sleeve parts 1, 2 are mounted one inside the other so as to be axially displaceable but fixed in terms of rotation. The fixing in terms of rotation can be obtained by ribs which extend in the direction of the central longitudinal axis 4 on the outside of the sleeve part 1 and engage in corresponding grooves in the inside face of the sleeve part 2. A nut 10 is provided for the axial displacement of the two sleeve parts 1, 2. This nut is constructed in the form of a tube section which, at its lower end, carries a radially outwardly extending flange 12 that rests on the inside face of the second sleeve part 2. The nut 10 has an external thread 13 which engages in an internal thread 14 of the first sleeve part 1. The internal thread 14 runs almost the entire length of the sleeve part 1. The external thread 13 of the nut 10 has a corresponding length. It would, of course, also suffice if the sleeve part 1 were to have only a short internal thread section 14' at its lower end, extending across an area 15, for example. A short external thread section 13' at the upper end of the nut 10 would also be conceivable and could extend across an area 16, for example. The internal thread 14 of the sleeve part 1 would then be correspondingly longer, depending on the desired extent of the height adjustment of the implant.

A toothed ring 17, which is used to rotate the nut 10, is disposed on the top face of the flange 12. The flange 12 and the toothed ring 17 correspond to a crown wheel of a contrate gear. In the area of the toothed ring 17, the second sleeve part 2 has an access opening 18 extending radially therethrough. An operating instrument, which cooperates with the toothed ring 17 and which will be described in more detail below, can be inserted through this access opening 18. The sleeve part 1 is moved out of the sleeve part 2 and, if necessary, is also moved back in again, through rotation of the nut 10. The outward movement is expediently limited by a non-illustrated abutment. Further non-illustrated radial openings can be provided in the sleeve parts 1, 2 and in the nut 10 in order to permit filling of the inner space of the implant with bone replacement material or the like, when placed in the spinal column.

A further illustrative embodiment of a length-adjustable implant is shown in FIGS. 2 through 6. The two sleeve parts 101 and 102 have axially extending windows 24 opening out in their mutually facing end faces 22, 23 in the assembled state. Circumferential sections 25, 26 separating two respective adjacent windows 24 from one another fit axially displaceably into the windows 24 of the respective other sleeve part 101, 102. Play is provided between the circumferential sections 25, 26 such that the two sleeve parts 101, 102 fit in one another without wobbling, but nevertheless ensure easy displaceability.

The length is adjusted, or the sleeve part 101 is moved in and out, through the use of a nut 110 which is disposed coaxially inside the first sleeve part 101 and has an external thread 113 which engages in an internal thread 114 of the first sleeve part 101. The internal thread 114 of the first sleeve part 101 extends approximately from the lower end face 22 of the sleeve part 1 to an upper end face 27 of the latter.

The nut 110 has a sleeve-shaped construction, a length section 29 that carries the external thread 113 and a length section 30 that has no thread. The length section 29 or external thread 114 is disposed above the second sleeve part 102.

An end face of the length section 29 which faces downward or toward the sleeve part 102 in the assembled state, is constructed as a toothed ring 117. The external diameter of the toothed ring 117 is smaller than the external diameter of the external thread 113 and smaller than the internal diameter of the sleeve part 102. The external diameter of the thread 114 of the nut 110 is, by contrast, greater than the internal diameter of the sleeve part 102 and dimensioned in such a way that the thread 114 engages with the internal thread 113 of the first sleeve part 101.

An indent forming an annular groove 33 is disposed between the length section 29 and the length section 30. In order to permit axial securing of the nut 110 on the sleeve part 102, the latter has radially inwardly extending projections 34 which engage in the annular groove 33 of the nut 110. The projections 34 are disposed at the free end of the circumferential sections 26 in such a way that their top face is flush with the upper end face 23 of the circumferential sections 26. The main components of the implant, that is to say the sleeve part 101, the sleeve part 102 and the nut 110, are preferably made of metal. The circumferential sections 26 can, however, bend radially outward to a slight extent when the nut 110 is fitted, in such a way that the nut 110 can be inserted with its length section 30 into the sleeve part 102, with the projections 34 snapping into the annular groove 33.

Figure 7:
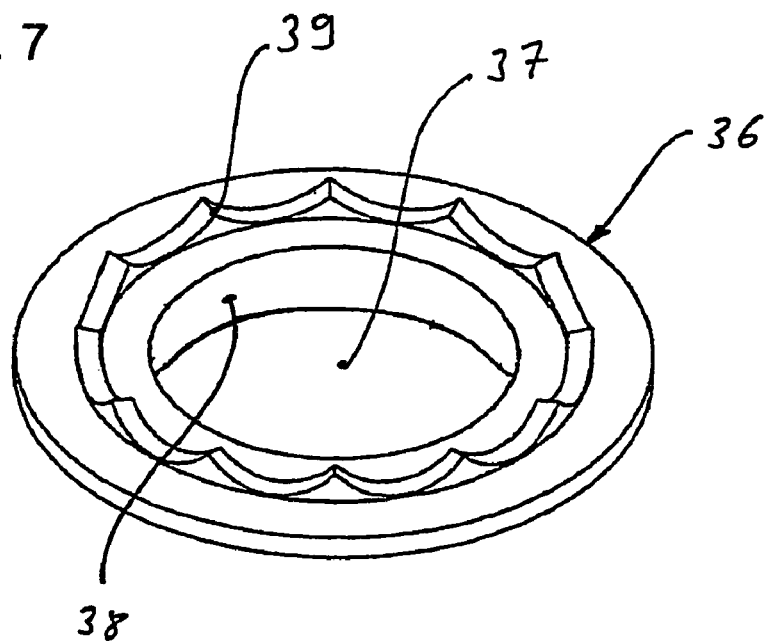
FIGS. 7 and 7A are perspective views of a support plate that can be secured on an implant.
Figure 7A:
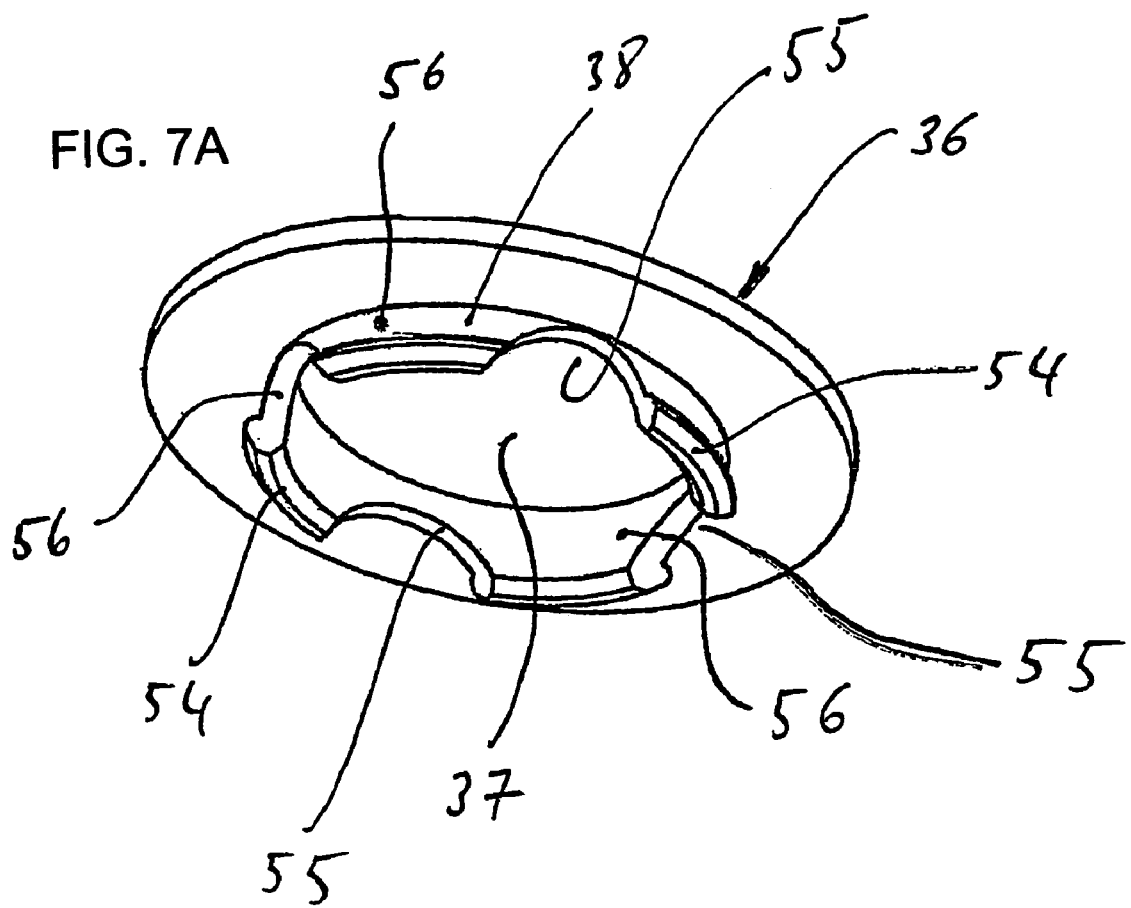

As is seen in FIGS. 7 and 7A, in order to increase the size of the support surface of the sleeve parts 101, 102, their end faces 27, 35 which are directed away from one another are provided with support plates 36 that protrude radially past the circumference of the sleeve parts 101, 102 and have a central opening 37 extending through them. The support plates 36 are preferably secured in a releasable manner. For this purpose, a skirt 38 delimiting the opening 37 is formed integrally on the underside of the support plate 36. This skirt 38 can, for example, have an external thread with which the support plate 36 can be screwed into the first sleeve part 101. In the embodiment according to FIGS. 7 and 7A, however, a snap-fit connection is provided. For this purpose, the inner face of one sleeve part 101, 102 is provided with an annular groove 121 (FIG. 10) into which it is possible to engage locking projections 54 that are formed integrally on the outer face of the skirt 38. The skirt 38 is divided into four circumferential sections 56 by recesses 55 disposed at the end face. The ends carrying the locking projections are deflected radially inward when a support plate 36 is inserted into a sleeve part 101, 102, but return to their original position, through the use of elastic restoring forces, when the locking projections 54 snap into the annular groove 121. The face of the support plate 36 directed away from the implant carries several projections in the form of a notched ring 39 which concentrically surrounds the opening 37. The notched ring 39 is used for fastening the implant on a vertebral body.

Figure 11:
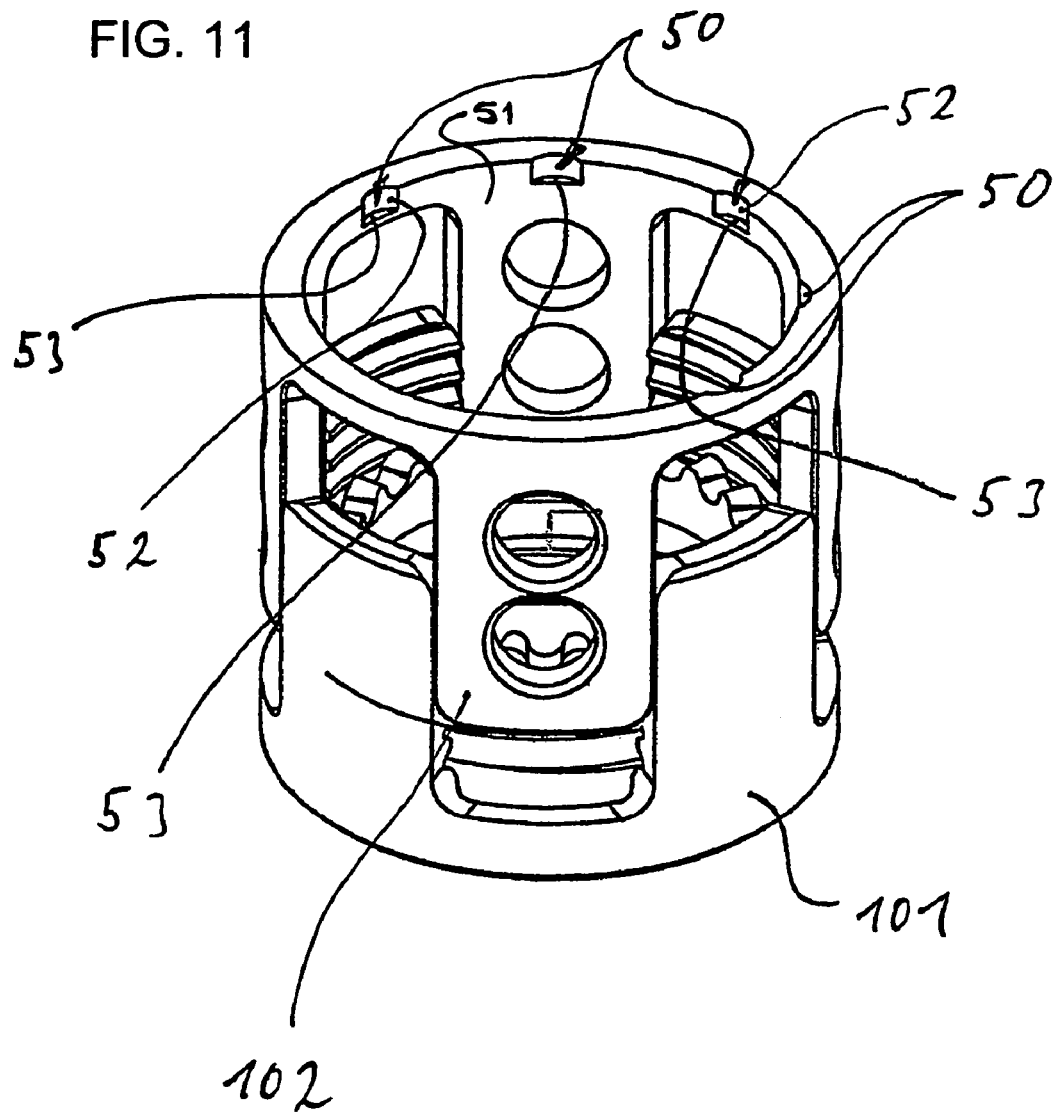
FIG. 11 is a perspective view of an implant which is modified as compared to FIG. 2.

FIGS. 11 and 12 show an illustrative embodiment in which a support plate 36a is secured in a rotationally fixed manner on at least one end face of a sleeve part 101, 102. For this purpose, recesses 50 are provided in the end faces 27, 35 of the sleeve parts 101, 102 and are distributed uniformly about the circumference of one sleeve part 101, 102. The recesses 50 extend in the axial direction and open into inside faces 51 of the sleeve parts. The recesses 55 are delimited by a curved inner wall 52 and a radial wall 53. In the assembled state, projections 57 of complementary shape, formed on the outer face of the skirt 38 or of the circumferential sections 56, engage in the recesses.

Figure 9:
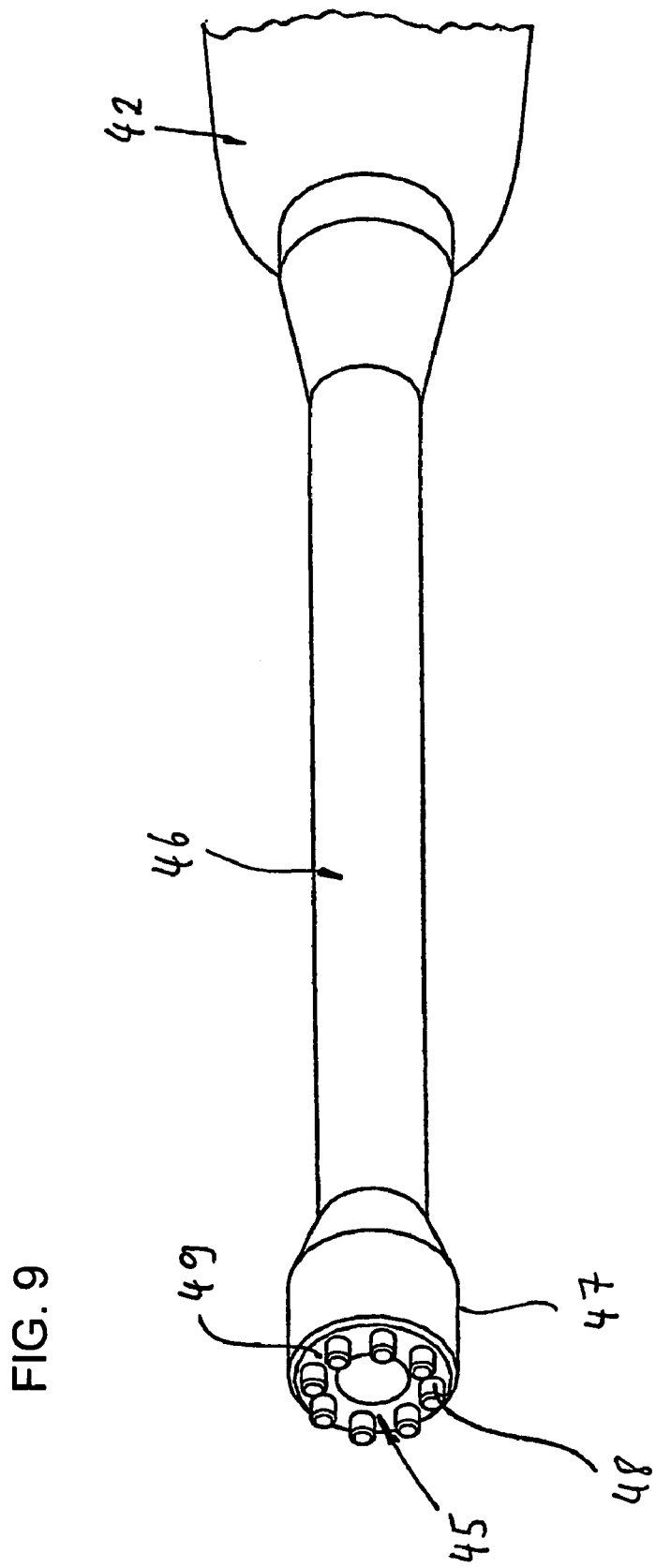
FIG. 9 is an enlarged, fragmentary, perspective view of the operating instrument shown in FIG. 8.

As is seen in FIGS. 2-5, 10 and 11, two openings 40 through which bone material or bone replacement material can be introduced into the inner space of the implant, are formed in the sleeve part 102, or its circumferential sections 26. It is, of course, possible for a different number of openings to be provided. These openings can also be present in the sleeve part 101. At least one of these openings forms an access opening 118 for an operating instrument, which will be described in more detail below. The toothed ring 117 protrudes into the cross section of the access opening 41. FIGS. 8 and 9 show an operating instrument including, as its main components, an elongate hand grip 42, a shaft 43 passing centrally through the latter in the longitudinal direction, a rotary grip 44 secured at an end of the shaft and a toothed wheel 45 secured at another end of the shaft. A section of the shaft 43 extending between the hand grip 42 and the toothed wheel 45 runs inside a jacket tube 46 having an end directed away from the toothed wheel 45 which is secured on the hand grip 42. A free end 47 of the jacket tube 46 is widened radially. The teeth of the toothed wheel 45 are pins 48 which protrude in the longitudinal direction of the shaft 43 from a front end face of a disk 49 fixed on the latter.

The operating instrument is inserted with its free end 47 into the access opening 18 or 118 in order to drive the nut 10 or 110. The pins 48 come into engagement with the toothed ring 17 or 117. This kind of toothed engagement is relatively robust and remains reliable and secure against blockage even when material gets into the area of the toothing. The free end 47 can be fixed in the access opening 18, 118 purely by frictional engagement. It is therefore conceivable for the free end 47 to be screwed with an external thread into an internal thread 122 (see FIG. 10) of the access opening 18, 118.

Figure 10:
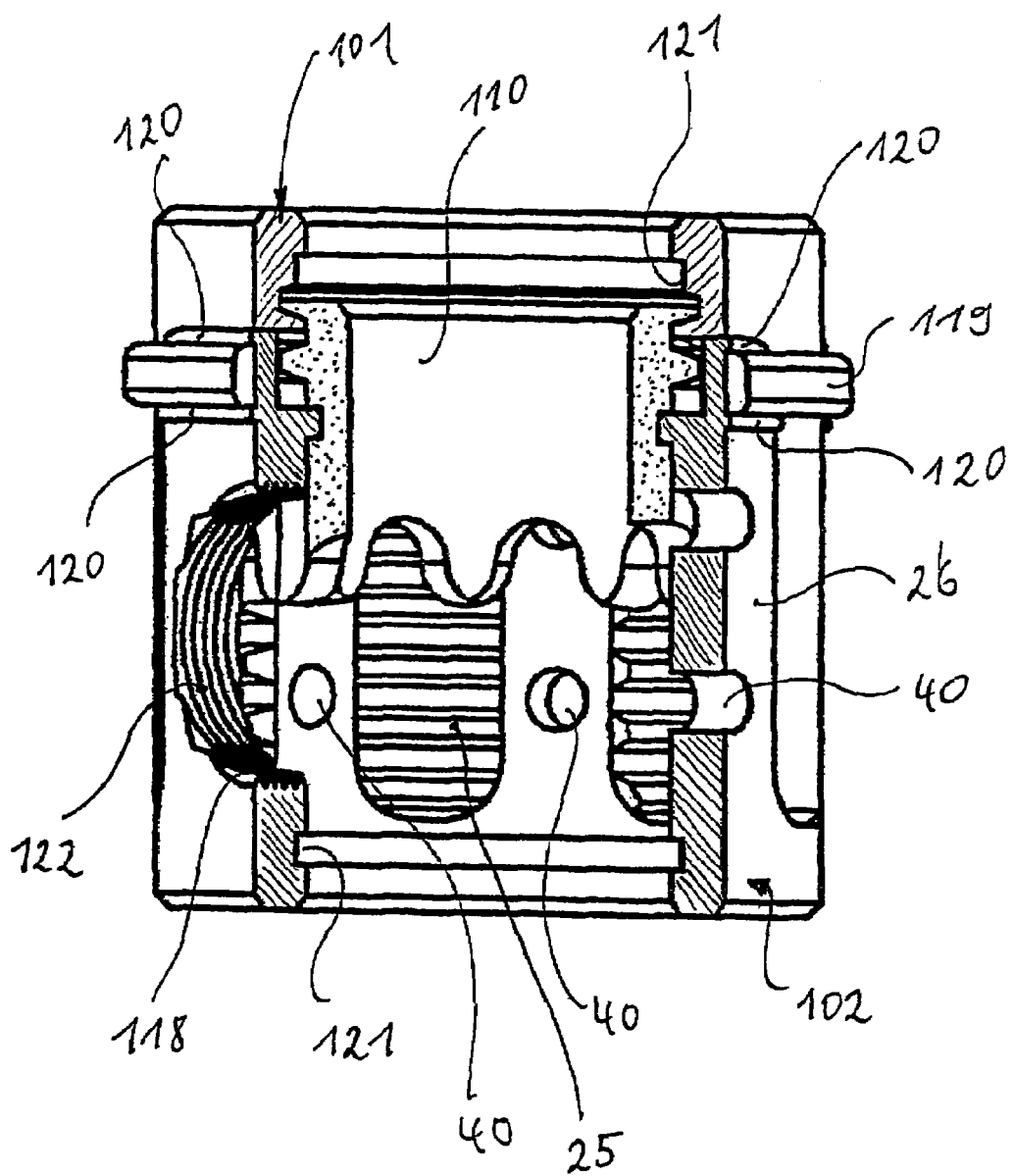
FIG. 10 is an opened and cross-sectional side view of an illustrative embodiment of an implant with a reinforcing ring.

FIG. 10 shows an illustrative embodiment with a reinforcing ring 119. The latter is disposed at the upper end of the circumferential section 26 of the second sleeve part 102. Ribs 120 protrude in the axial direction from the outer circumferential surface of the circumferential sections 26 and receive the reinforcing ring 119 between them and fix it in the axial direction. The reinforcing ring 119 makes it possible to reduce the wall thickness of the circumferential sections 26 of the second sleeve part 102 and also the circumferential sections 25 of the first sleeve part 101, without any danger of the circumferential sections 25, 26 being bent radially outward when subjected to pressure.

In the illustrative embodiment according to FIG. 10, grooves 121 are worked into corresponding inner circumferential surfaces in the upper end area and lower end area of the sleeve parts 101, 102. The support plate 36 can be fixed into the grooves 121 in the manner of a snap-fit connection. Grooves 121 can also be present in the illustrative embodiments that were described in further detail above.

The access opening 118 has an internal thread 122 into which an operating instrument can be screwed. The illustrative embodiment according to FIG. 10 also shows that the access opening 118 can have a larger diameter than the other openings 40 in the circumferential sections 25, 26.

I Claim:

1. A height-adjustable implant for insertion between vertebral bodies, the implant comprising:
   a first sleeve part having an internal thread;
   a second sleeve part;
   said first and second sleeve parts:
      being coaxially oriented about a central longitudinal axis;
      being connected to one another in a rotationally fixed and axially displaceable manner;
      having axially extending windows therein with mutually-facing, outwardly-open ends;
   each adjacent two of said windows defining a respective circumferential section therebetween in each of said sleeve parts;
   said circumferential sections of each one of said sleeve parts each fitting axially displaceably into a respective one of said windows of the other of said sleeve parts and defining an inner space of the implant, at least one of said circumferential sections of said second sleeve part having an access opening formed radially therethrough;
   a nut disposed coaxially and circumferentially contained within said inner space and secured on said second sleeve part in a rotatable but axially fixed manner, said nut having an external thread engaging in said internal thread of said first sleeve part, said nut being secured on said second sleeve part with said external thread located outside said second sleeve part, as seen in an axial direction, said nut having an outer surface with an annular groove formed therein, said circumferential sections of said second sleeve part each have an inside face with a radially inwardly extending projection engaging in said annular groove of said nut; and
   a toothed ring extended coaxially relative to said central longitudinal axis and disposed on said nut partially covering said access opening and on a side of said nut facing toward said second sleeve part, said access opening configured for receiving an operating instrument which cooperates with said toothed ring.

2. The implant according to claim 1, wherein said toothed ring is constructed as a crown wheel of a contrate gear.

3. The implant according to claim 1, wherein said toothed ring is disposed on a surface of said nut facing away from said external thread.

4. The implant according to claim 1, wherein said circumferential sections have free ends, and said projections are disposed near said free ends.

5. The implant according to claim 1, wherein said first and second sleeve parts each have an end face intended to bear on a vertebral body, and a respective support plate is secured on said end face of at least one of said sleeve parts.

6. The implant according to claim 5, wherein said support plate is releasably secured on said end face.

7. The implant according to claim 6, wherein said support plate is secured in a rotationally fixed manner on one of said sleeve parts.

8. The implant according to claim 7, wherein:
said sleeve parts each have an end face and an inside face;
said end face of at least one of said sleeve parts has a plurality of circumferentially spaced-apart recesses formed therein opening into said inside face of said at least one of said sleeve parts; and
said support plate has projections complementary in shape to and engaging in said recesses.

9. The implant according to claim 5, wherein said support plate is secured in a rotationally fixed manner on one of said sleeve parts.

10. The implant according to claim 9, wherein:
said sleeve parts each have an end face and an inside face;
said end face of at least one of said sleeve parts has a plurality of circumferentially spaced-apart recesses formed therein opening into said inside face of said at least one of said sleeve parts; and
said support plate has projections complementary in shape to and engaging in said recesses.

11. The implant according to claim 1, wherein said first and second sleeve parts have substantially the same diameter.

12. The implant according to claim 1, wherein said respective circumferential sections have substantially the same wall thickness.

* * * * *